US008545410B2

(12) United States Patent
Hope Simpson et al.

(10) Patent No.: US 8,545,410 B2
(45) Date of Patent: Oct. 1, 2013

(54) METHOD AND SYSTEM OF STRAIN GAIN COMPENSATION IN ELASTICITY IMAGING

(75) Inventors: David Hope Simpson, Bothell, WA (US); Unmin Bae, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 324 days.

(21) Appl. No.: 12/808,711

(22) PCT Filed: Dec. 16, 2008

(86) PCT No.: PCT/IB2008/055355
§ 371 (c)(1),
(2), (4) Date: Jun. 17, 2010

(87) PCT Pub. No.: WO2009/077985
PCT Pub. Date: Jun. 25, 2009

(65) Prior Publication Data
US 2010/0292572 A1    Nov. 18, 2010

Related U.S. Application Data

(60) Provisional application No. 61/014,083, filed on Dec. 17, 2007.

(51) Int. Cl.
*A61B 8/00* (2006.01)
(52) U.S. Cl.
USPC .......................................... 600/442; 600/437
(58) Field of Classification Search
USPC .................................................. 600/437–469
See application file for complete search history.

(56) References Cited

U.S. PATENT DOCUMENTS

| 5,265,612 | A | * | 11/1993 | Sarvazyan et al. | 600/471 |
|---|---|---|---|---|---|
| 5,524,636 | A | * | 6/1996 | Sarvazyan et al. | 600/587 |
| 5,606,971 | A | * | 3/1997 | Sarvazyan | 600/438 |
| 5,678,565 | A | * | 10/1997 | Sarvazyan | 600/587 |
| 5,810,731 | A | * | 9/1998 | Sarvazyan et al. | 600/438 |
| 6,099,471 | A | * | 8/2000 | Torp et al. | 600/438 |
| 6,494,834 | B2 | * | 12/2002 | Konofagou et al. | 600/438 |
| 6,517,485 | B2 | * | 2/2003 | Torp et al. | 600/438 |
| 6,676,599 | B2 | * | 1/2004 | Torp et al. | 600/437 |
| 7,077,807 | B2 | * | 7/2006 | Torp et al. | 600/438 |
| 7,640,051 | B2 | * | 12/2009 | Krishnan et al. | 600/407 |

(Continued)

FOREIGN PATENT DOCUMENTS

| EP | 1762180 A | 3/2007 |
|---|---|---|
| EP | 1800603 A | 6/2007 |

(Continued)

*Primary Examiner* — Sanjay Cattungal

(57) ABSTRACT

A method and system of strain gain compensation in elasticity imaging is provided. The system can include a probe (120) for transmitting ultrasonic energy into a physiology (150) of a patient (50) and receiving echoes, a display device (170), and a processor (100) operably coupled to the probe and the display device. The processor can process ultrasound imaging data associated with an applied stress of the physiology of the patient. The processor can generate a strain compensation function associated with the applied stress based on at least one of (i) user inputs based on expected results associated with a portion of the physiology, (ii) a strain compensation model generated prior to processing the ultrasound imaging data, and (iii) at least a portion of the imaging data. The processor can apply the strain compensation function to the imaging data to generate a compensated strain image. The processor can present on the display device at least one of the compensated strain image and an inverse of the compensated strain image. Other embodiments are disclosed.

20 Claims, 8 Drawing Sheets

(56) References Cited

U.S. PATENT DOCUMENTS

| | | | |
|---|---|---|---|
| 7,905,835 B2 * | 3/2011 | Perrey et al. | 600/438 |
| 8,041,415 B2 * | 10/2011 | Shiina et al. | 600/433 |
| 8,098,921 B2 * | 1/2012 | Matsumura | 382/133 |
| 8,100,831 B2 * | 1/2012 | Hiltawsky et al. | 600/438 |
| 8,235,898 B2 * | 8/2012 | Bae et al. | 600/437 |
| 2005/0049497 A1 * | 3/2005 | Krishnan et al. | 600/437 |
| 2006/0025682 A1 * | 2/2006 | Vanderby et al. | 600/438 |
| 2006/0052696 A1 * | 3/2006 | Shiina et al. | 600/437 |
| 2007/0073145 A1 | 3/2007 | Fan et al. | |
| 2007/0083116 A1 * | 4/2007 | Sato | 600/437 |
| 2007/0112270 A1 * | 5/2007 | Waki et al. | 600/455 |
| 2008/0081994 A1 * | 4/2008 | Kim et al. | |
| 2008/0119732 A1 * | 5/2008 | Hiltawsky et al. | 600/438 |
| 2008/0287792 A1 * | 11/2008 | Bae et al. | 600/438 |
| 2009/0124903 A1 * | 5/2009 | Osaka | 600/443 |
| 2009/0131797 A1 * | 5/2009 | Jeong et al. | 600/459 |
| 2009/0182234 A1 * | 7/2009 | Perrey et al. | 600/443 |
| 2009/0326378 A1 * | 12/2009 | Lee et al. | 600/447 |
| 2010/0121178 A1 * | 5/2010 | Krishnan et al. | 600/411 |
| 2010/0220901 A1 * | 9/2010 | Matsumura | 382/128 |
| 2010/0292572 A1 * | 11/2010 | Hope Simpson et al. | 600/438 |
| 2010/0324421 A1 * | 12/2010 | Waki et al. | 600/443 |
| 2011/0125019 A1 * | 5/2011 | Shiina et al. | 600/443 |

FOREIGN PATENT DOCUMENTS

| | | |
|---|---|---|
| EP | 1810620 A | 7/2007 |
| JP | 2001519674 A | 10/2001 |
| JP | 2007044231 | 2/2007 |
| WO | 2006026008 A2 | 3/2006 |

* cited by examiner

METHOD AND SYSTEM OF STRAIN GAIN COMPENSATION IN ELASTICITY IMAGING

This application is the national stage entry of and claims the priority of international patent application number PCT/IB2008/055355, filed Dec. 16, 2008, which claims the benefit of U.S. provisional application No. 61/014,083, filed Dec. 17, 2007.

This disclosure relates generally to imaging systems and more specifically to a method and system for elasticity imaging.

Elasticity imaging consists of inducing motion in a biological tissue and evaluating the response of the tissue using diagnostic imaging techniques. Elasticity imaging can be used to reveal the mechanical properties of the tissue, such as Poisson's Ratio, Young's Modulus or other stiffness measurements. The measurements can provide an array of data in which array locations correspond to tissue locations in an image plane. The array of data may be mapped to a gray scale or a color map to form a picture. Elasticity imaging can include capturing the data during externally or internally applied tissue motion or deformation; evaluating tissue response, and presenting an image representative of the tissue property.

Elasticity imaging techniques can be categorized into two groups based on tissue excitation techniques. Static methods use quasistatic compression and estimate resulting tissue strain. Stiff tissue shows less strain than softer tissue under applied force. Thus, by estimating tissue strain induced by compression, tissue stiffness information can be obtained. The estimated strain can also be used for reconstruction of the tissue elasticity modulus. The other category is based on inducing a dynamic excitation in tissue (dynamic method). In sonoelasticity, low frequency vibration (<1 kHz) is applied to tissues, and the tissue response is inspected. Another approach in this category is acoustic remote palpation where acoustic radiation force is applied in a local tissue area, and the resulting displacement is estimated.

In elasticity imaging, the ultrasound data before and after the compression is recorded to determine axial and lateral motions using correlation methods. The determined motions along the ultrasound propagation direction represent the axial displacement map of the tissue and are used to determine the axial strain map. The strain map is then displayed as a gray scale or color-coded image and is called an elastogram.

However, the applied stress during elasticity imaging can be non-uniform within the image plane. This can result in a strain image with variable appearance over the field of view even for tissue with uniform stiffness. For example, the strain image can vary with depth in uniform tissue due to stress decay over depth. This can mislead users to perceive that the strain variation is due to a variation in tissue stiffness.

Thus, there is a need for a method and system for compensating for the strain variation that is not caused by the actual stiffness variation in tissue. There is yet a further need for such a method and system that presents images with more easily recognizable differences between normal tissue and lesions. There is yet a further need for such a method and system that provides more easily recognized local areas of abnormal strain.

The Summary is provided to comply with 37 C.F.R. §1.73, requiring a summary of the invention briefly indicating the nature and substance of the invention. It is submitted with the understanding that it will not be used to interpret or limit the scope or meaning of the claims.

In one exemplary embodiment of the present disclosure, a method of elasticity imaging is provided. The method can include transmitting ultrasonic energy and receiving echoes therefrom; processing imaging data from the echoes associated with an applied stress of a physiology of a patient; obtaining a strain compensation function associated with the applied stress; applying the strain compensation function to the imaging data to generate a compensated strain image; and presenting the compensated strain image.

In another exemplary embodiment, a computer readable storage medium in which computer-executable code is stored, is provided. The computer-executable code is configured to cause a computing device in which the computer-readable storage medium is loaded to execute the steps of: processing ultrasound imaging data associated with an applied stress of a physiology of a patient; generating a strain compensation function associated with the applied stress based on at least one of (i) user inputs based on expected results associated with a portion of the physiology, (ii) a strain compensation model generated prior to processing the ultrasound imaging data, and (iii) at least a portion of the processed imaging data; and applying the strain compensation function to the imaging data to generate a compensated strain image.

In a further exemplary embodiment, an ultrasound imaging system is provided that can have a probe for transmitting ultrasonic energy into a physiology of a patient and receiving echoes, a display device, and a processor operably coupled to the probe and the display device. The processor can process ultrasound imaging data associated with an applied stress of the physiology of the patient. The processor can generate a strain compensation function associated with the applied stress based on at least one of (i) user inputs based on expected results associated with a portion of the physiology, (ii) a strain compensation model generated prior to processing the ultrasound imaging data, and (iii) at least a portion of the processed imaging data. The processor can apply the strain compensation function to the imaging data to generate a compensated strain image. The processor can present on the display device at least one of the compensated strain image and an inverse of the compensated strain image.

The technical effect includes, but is not limited to, presenting images that qualitatively highlight elastic differences in the physiology of a body. The technical effect further includes, but is not limited to, presenting images that highlight differences between normal tissue and lesions. The technical effect yet further includes, but is not limited to, presenting images that highlight localized areas of abnormal strain.

The above-described and other features and advantages of the present disclosure will be appreciated and understood by those skilled in the art from the following detailed description, drawings, and appended claims.

The exemplary embodiments of the present disclosure are described with respect to data capture and imaging of a body performed by an ultrasound imaging device based on strain being examined with respect to a physiology of the body. It should be understood by one of ordinary skill in the art that the exemplary embodiments of the present disclosure can be applied to various portions of the body and various physiology, whether human or animal, such as tissue, organs, and so forth, including the liver. The applied stress resulting in the examined strain of the present disclosure can be external or internal to the body. The source of the applied stress can vary, such as generated from pressing down with the transducer, generated by a separate device, generated by application of wave propagation through the tissue, or created by the body itself, including arterial pulsations or respiratory variations in the patient. The amount and/or timing of the applied stress can also vary, including periodically applied stress that is qualitatively examined according to the exemplary embodiments of the present disclosure.

The exemplary embodiments of the present disclosure can provide a more uniform strain image, such as for homogeneous tissue over a field of view, or a portion thereof, of the ultrasound system, and can highlight various physiological differences, such as between normal tissue and lesions. In one embodiment, an elastographic image can be generated by normalizing the strain image with a modified or estimated stress. The modified or estimated stress can be user-generated and/or system-generated as will be described later.

The strain being examined is related to the stress and the elastic modulus of the tissue as follows:

$$\text{Strain}(X,Y)=\text{Stress}(X,Y)/(\text{Elasticity Modulus}(X,Y)) \quad (1)$$

or, equivalently:

$$\text{Strain}(X,Y)/\text{Stress}(X,Y)=1/(\text{Elasticity Modulus}(X,Y)) \quad (2)$$

A modification or estimate of the stress can be generated, SC(X,Y), for the applied stress. The modified stress, SC(X,Y), can then be used to generate an estimate of the elastic modulus distribution as follows:

$$(1/\text{Elastic Modulus}(X,Y))\propto(\text{Strain}(X,Y)/SC(X,Y)) \quad (3)$$

or, equivalently:

$$(\text{Elastic Modulus}(X,Y))\propto(SC(X,Y)/\text{Strain}(X,Y)) \quad (4)$$

The present disclosure contemplates that a compensated strain image generated according to an exemplary embodiment of the present disclosure can provide normal tissue with a more uniform appearance than an uncompensated strain image, helping to highlight localized areas of abnormal strain. The qualitative results provided by the compensated strain image of the present disclosure can be applicable even where the modified stress SC(X,Y) deviates significantly from the actual stress distribution in tissue.

Figure 1:
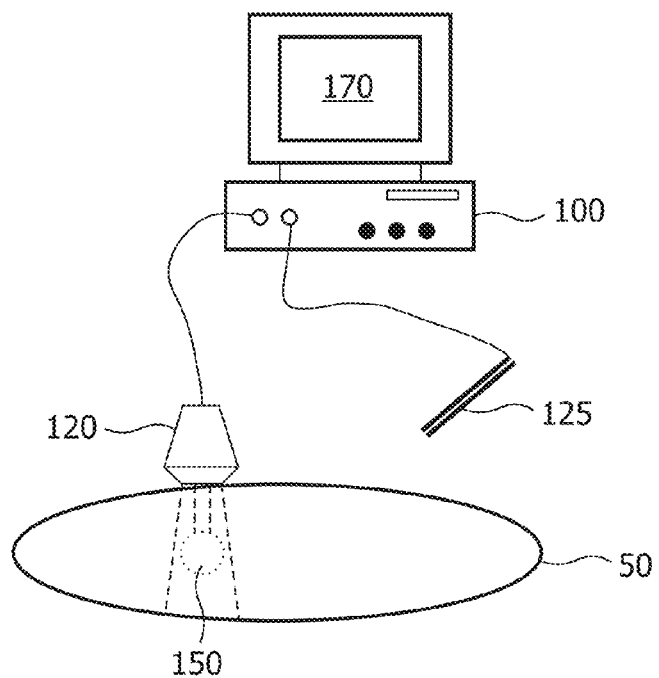
FIG. 1 is a schematic illustration of a system for performing elastic imaging according to an exemplary embodiment of the present invention.

Referring to the drawings, and in particular to FIG. 1, an ultrasound imaging system in accordance with one exemplary embodiment of the invention is shown and generally represented by reference numeral 10. The system 10 can perform ultrasound imaging on a patient's body 50, such as of an organ or tissue 150, and can include a processor or other control device 100, a probe or transducer 120, and a display device 170. The system 10 can include a stress device 125 for generating and applying the stress to the body 50. The stress device 125 can be an externally and/or internally used device, and can provide the applied stress to the region of interest in a number of different ways, including energy wave propagation or mechanically generated forces.

Figure 2:
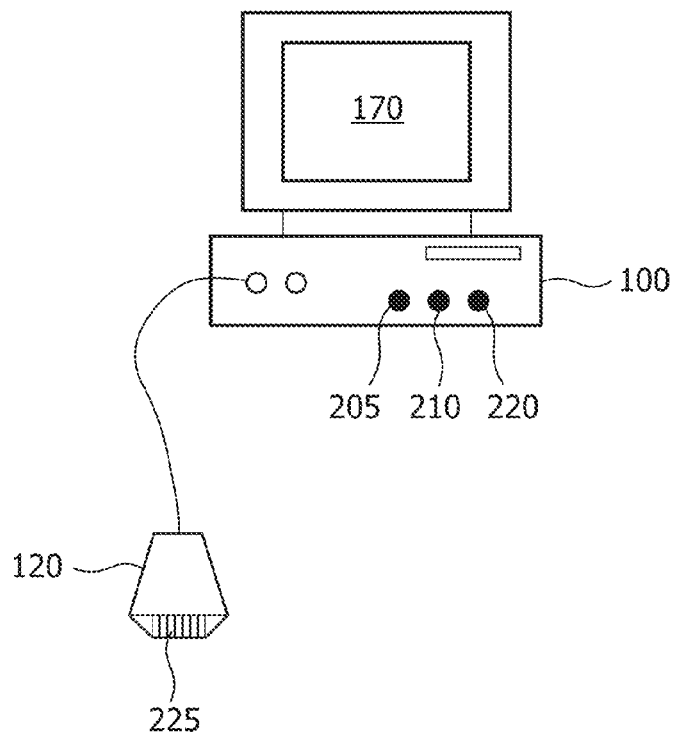
FIG. 2 is a schematic illustration of a portion of the system of FIG. 1.

Referring additionally to FIG. 2, the processor 100 can include various components for performing ultrasound imaging, and can employ various imaging techniques, such as with respect to data capture, analysis and presentation. For example, the processor 100 can include a strain function control or actuator 205 to adjust the strain compensation function, as will be described later. The processor 100 can also include a time-gain compensation control or actuator 210, and a lateral-gain compensation control or actuator 215, as well as other ultrasound components, such as a transmitter/receiver, a beamformer, an echo processor, and a video processor. The present disclosure also contemplates one or more of these components being combined.

In one embodiment, the ultrasonic probe 120 can include a linear array of ultrasonic transducer elements 225 which transmit and receive the ultrasonic energy, such as under the control of the beamformer. For example, the beamformer can control the timing of actuation of the transducer array elements 225 by activating transducer pulsers of the transmitter/receiver at appropriate times. In another embodiment, the probe 120 can be a matrix array transducer that provides a steered and focused ultrasonic beam.

The display device 170, such as with the assistance of the video processor, can then be used to present the image generated by the processor 100. Various other components and techniques can be utilized by system 10 for generating, transmitting and receiving ultrasonic energy, as well as for processing the received ultrasonic energy. The components and techniques of system 10 allow for presentation of a strain image in 2D or 3D on the display device 170 of a region of interest of the body 50. In one embodiment, the system 10 can also include a memory device, such as a CINELOOP® memory. For example, the memory device can store data processed by the system 10 to form a first strain image or image stream so that subsequent strain images or image streams can be generated therefrom. Other components and/or techniques can also be used with the processor 100, such as an automatic border detection processor that can define and graphically overlay anatomical borders with respect to the images presented. The present disclosure also contemplates the use of other components and/or techniques in addition to, or in place of, the components of system 10 described above.

Figure 3:
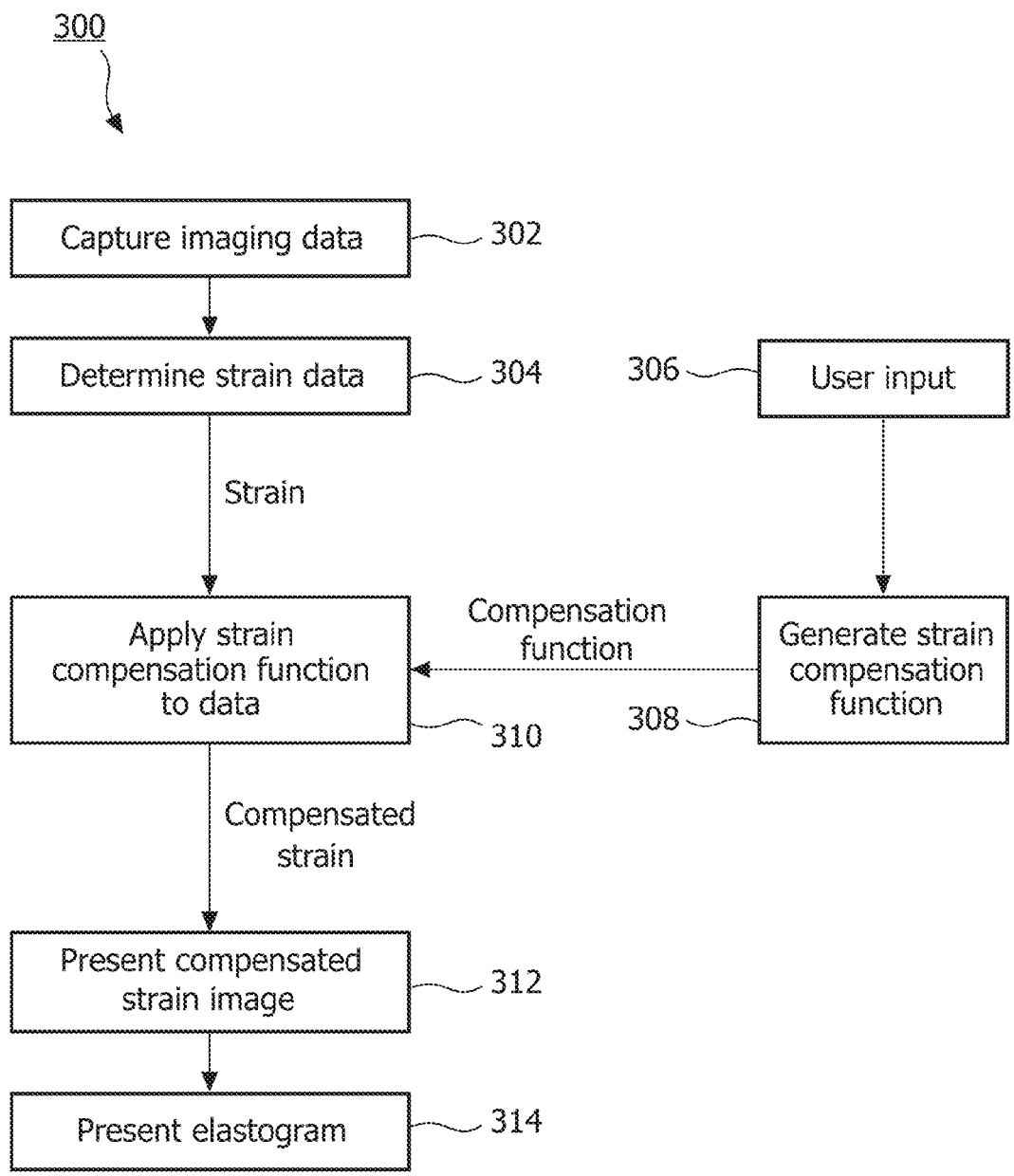
FIG. 3 is a method that can be used by the system of FIG. 1 for performing elastic imaging according to an exemplary embodiment of the present invention.

Referring additionally to FIG. 3, an exemplary method of operation of the system 10 is shown and generally represented by reference numeral 300. It would be apparent to one of ordinary skill in the art that other embodiments not depicted in FIG. 3 are possible without departing from the scope of the claims described below, including examination of other portions of the body.

Method 300 can begin with step 302 in which imaging data is captured by system 10, such as through the transmission and reception of ultrasonic energy or pulses by the probe 120 in combination with an applied stress in a region of interest. As described above, the applied stress can be provided by a number of sources, including applying pressure at the skin level of the body using the transducer probe 120 or as created by the body itself, such as cardiac pulsations or respiratory variations. In step 304, the strain resulting from the applied stress can be determined from the data that was captured.

In step 306, the system 10 can monitor for user input of an adjustment to the strain compensation function by a clinician or other user, such as through rotation or other adjustment of the strain compensation function control 205. If an adjustment to the strain compensation function is detected then a strain compensation function can be generated or otherwise adjusted as in step 308. In one embodiment, the strain compensation function can initially be set at unity so that the strain image is initially presented as an uncompensated strain image.

The adjustment to the strain compensation function can be to a magnitude of the strain compensation function as a function of depth. The present disclosure also contemplates the adjustment to the strain compensation function being a function of lateral and/or elevation positions. In one embodiment, a clinician or other user can adjust the strain compensation function based on expected results, such as by adjustment until tissues or other physiology with expected uniform properties appear substantially uniform on the presented image. In another embodiment, the adjustment to the strain compensation function can be based on the clinician's or other user's subjective view of the real-time image or image stream and known physiology in a localized area of the image so that a qualitative image can be presented with respect to other areas of the image that do not have uniform properties.

The present disclosure contemplates the adjustment to the strain compensation function being performed at various times. For example, the adjustment can be in real-time as described above or the data captured can be presented in a loop and the clinician can make the adjustment during the loop presentation, such as during or shortly after the patient's examination.

The strain compensation function can be applied to the determined strain data or any subsequent determination of the strain, as in step 310. In step 312, a compensated strain image can be presented, such as on display device 170. In step 314, after the strain compensation function has been adjusted as desired based on known or expected localized results and the compensated strain image presented, an elastogram or other print-out can be presented, such as of other data generated based on the compensated strain image.

Figure 4:
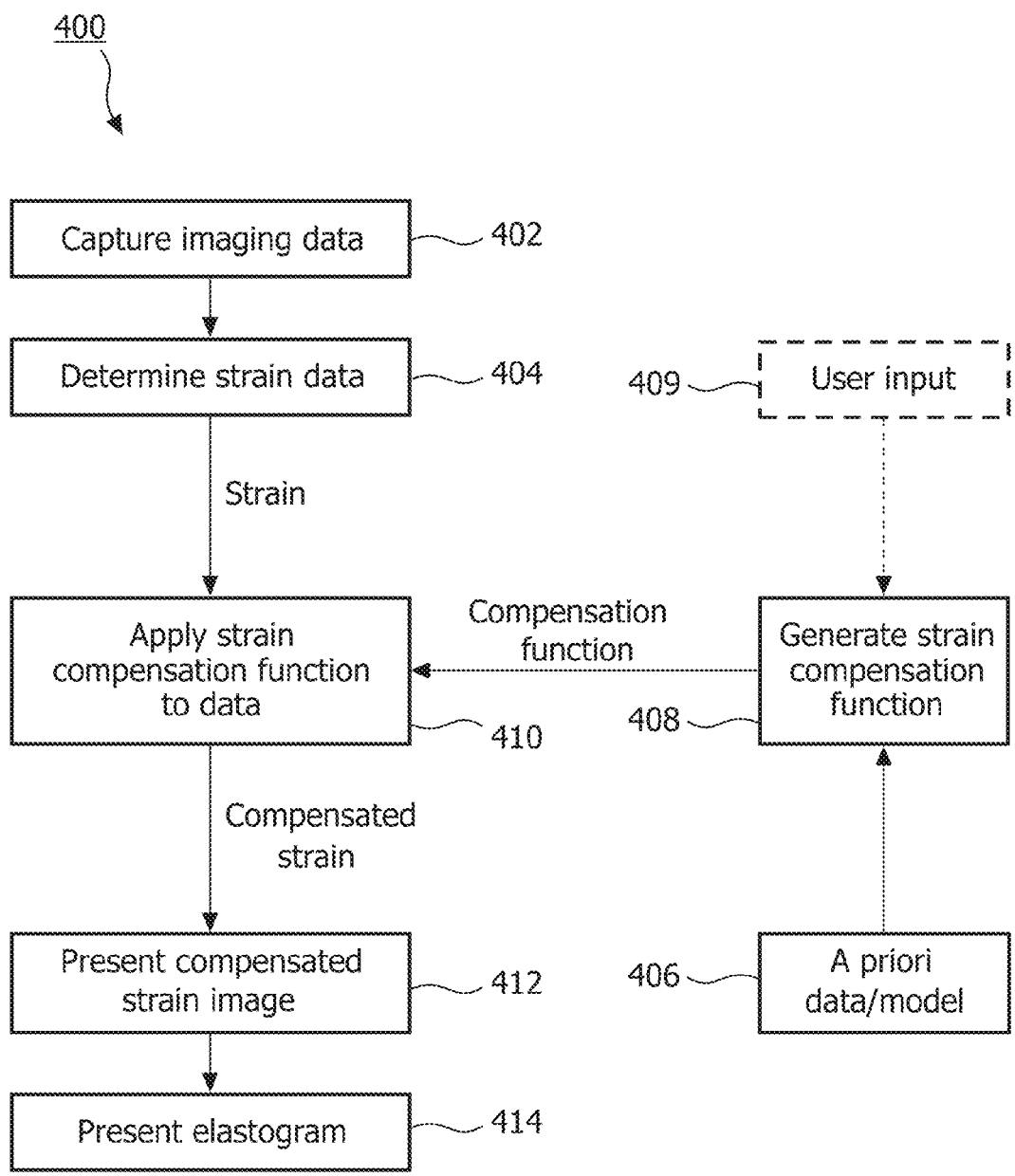
FIG. 4 is a method that can be used by the system of FIG. 1 for performing elastic imaging according to another exemplary embodiment of the present invention.

Referring to FIGS. 1-2 and 4, an exemplary method of operation of the system 10 is shown and generally represented by reference numeral 400. It would be apparent to one of ordinary skill in the art that other embodiments not depicted in FIG. 4 are possible without departing from the scope of the claims described below, including examination of other portions of the body. For example, possible variants to method 400 are shown in broken lines.

Method 400 can begin with step 402 in which imaging data is captured by system 10, such as through the transmission and reception of ultrasonic energy or pulses by the probe 120 in combination with an applied stress in a region of interest. In step 404, the strain resulting from the applied stress can be determined from the data that was captured or otherwise retrieved.

In step 406, a strain compensation function model can be obtained and applied to the captured data. The strain compensation function model can be generated or otherwise obtained using a number of techniques. For example, the strain compensation function model can be modeled mathematically, set empirically during optimization with the same or other patients using physiology with known properties, and/or measured on a uniform tissue-mimicking phantom or other physical model for the particular physiology to be imaged. The strain compensation function model may then be stored and applied to subsequent imaging examinations for the same or different patients. In one embodiment, the choice of which model to apply can be based on a number of factors, such as the type of physiology being examined, the age of the patient, and so forth.

A strain compensation function can be generated or otherwise adjusted based on the a priori strain compensation function model, as in step 408. In one embodiment, the strain compensation function can initially be set at unity so that the strain image is initially presented as an uncompensated strain image. In another embodiment, the system 10 in step 409 can monitor for an adjustment to the strain compensation function by a clinician or other user, such as through rotation or other adjustment of the strain compensation function control 205. If an adjustment to the strain compensation function is detected then the strain compensation function determined from the a priori model can be adjusted accordingly.

The strain compensation function can be applied to the determined strain data or any subsequent determination of the strain, as in step 410. In step 412, a compensated strain image can be presented, such as on display device 170. In step 414, after the compensated strain image has been presented, an elastogram or other print-out can be presented, such as of other data generated based on the compensated strain image.

Figure 5:
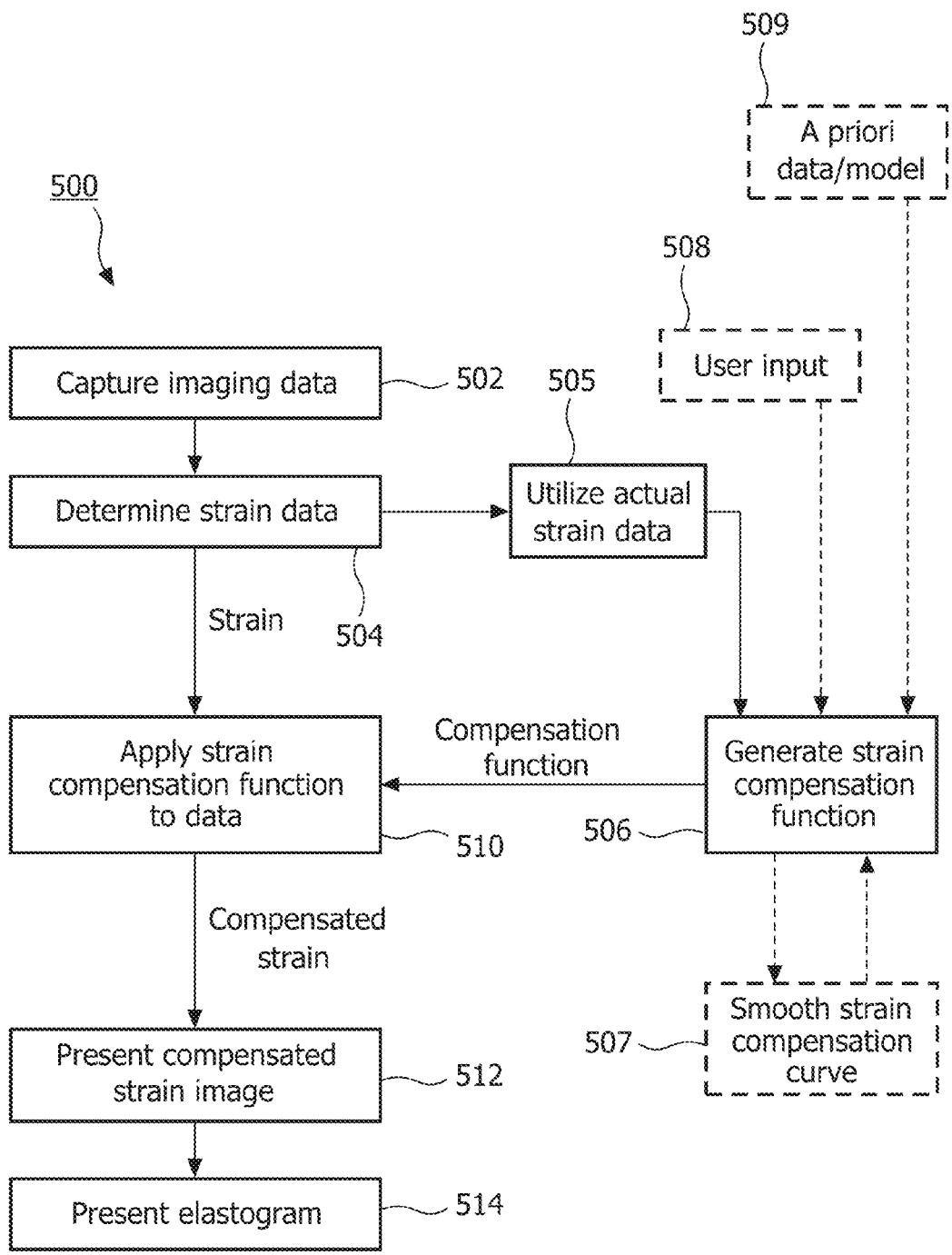
FIG. 5 is a method that can be used by the system of FIG. 1 for performing elastic imaging according to another exemplary embodiment of the present invention.

Referring to FIGS. 1-2 and 5, an exemplary method of operation of the system 10 is shown and generally represented by reference numeral 500. It would be apparent to an artisan with ordinary skill in the art that other embodiments not depicted in FIG. 5 are possible without departing from the scope of the claims described below, including examination of other portions of the body. For examples, possible variants to method 500 are shown in broken lines.

Method 500 can begin with step 502 in which imaging data is captured by system 10, such as through the transmission and reception of ultrasonic energy or pulses by the probe 120 in combination with an applied stress in a region of interest. In step 504, the strain resulting from the applied stress can be determined from the data that was captured or otherwise retrieved.

In steps 505 and 506, the captured data can be used to generate a strain compensation function. For example, the strain compensation function can be generated based on a median strain calculated as a function of depth. Setting the strain compensation function based on the median strain as a function of depth yields a normalized strain function.

The generated curve representative of the strain compensation function can be smoothed in step 507 so that there are no abrupt direction changes. In one embodiment, either or both of user input in step 508 or an a priori model as in step 509 can also be used in generating or otherwise adjusting the strain compensation function.

The strain compensation function can be applied to the determined strain data or any subsequent determination of the strain, as in step 510. In step 512, a compensated strain image can be presented, such as on display device 170, including in real-time or in a stream loop. In step 514, after the compensated strain image has been presented, an elastogram or other print-out can be presented, such as of other data generated based on the compensated strain image.

The method 500 contemplates other techniques and algorithms being utilized to generate a strain compensation function from the captured data, including lateral-gain compensation techniques. In one embodiment, two or more of the techniques described above with respect to methods 300, 400 and 500 can be applied to generate a compensated strain image.

Figure 6:
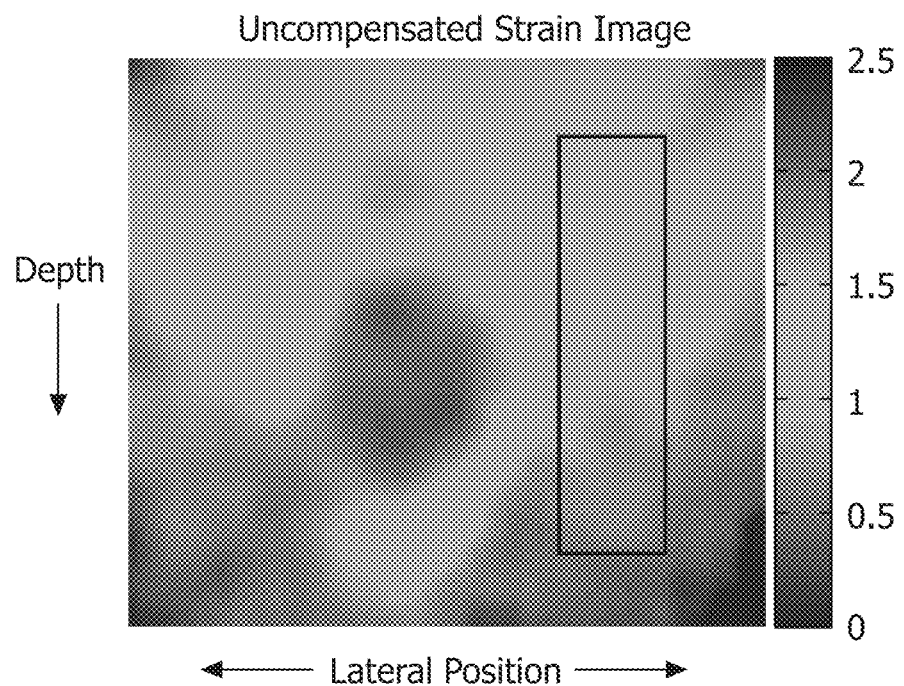
FIG. 6 is an elastogram showing an uncompensated strain image of a tissue with a hard inclusion.
Figure 7:
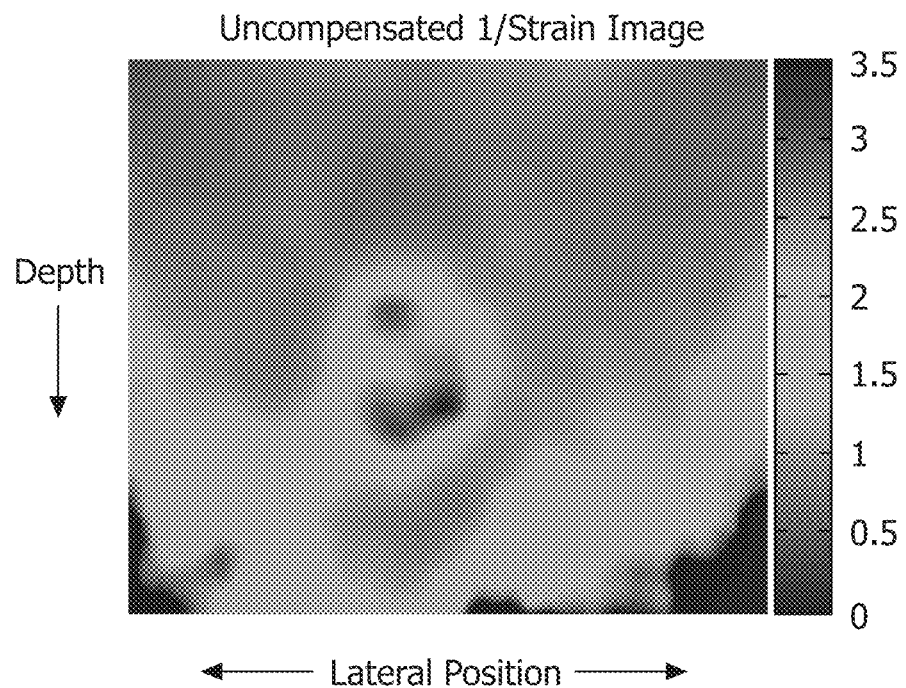
FIG. 7 is an elastogram showing the inverse of the uncompensated strain image of FIG. 6.

Referring to FIG. 6, an uncompensated strain image is shown which has a hard inclusion, with an elastic modulus of approximately three times the surrounding tissue, in a substantially uniform background tissue. In this example, the applied stress was generated by pushing a linear array transducer in the depth direction in a tissue mimicking phantom or model, but the results are applicable to application on actual tissue. As can be seen in the rectangular selection of FIG. 6, even in the uniform tissue surrounding the inclusion, the strain varies with depth due to depth-dependent variation in the applied stress. In FIG. 7, the mathematical inverse of the uncompensated strain image of FIG. 6 is shown and again indicates large variations of strain, even in regions of the similar tissue properties.

Figure 8:
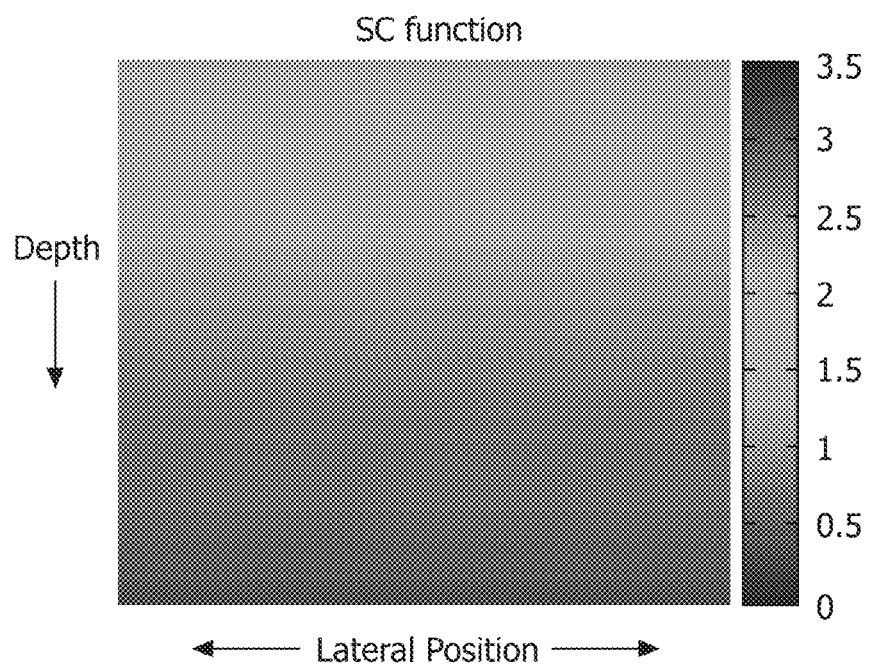
FIG. 8 is an image of one of a number of exemplary strain compensation functions generated according to the system or methods of FIGS. 1-5.
Figure 9:
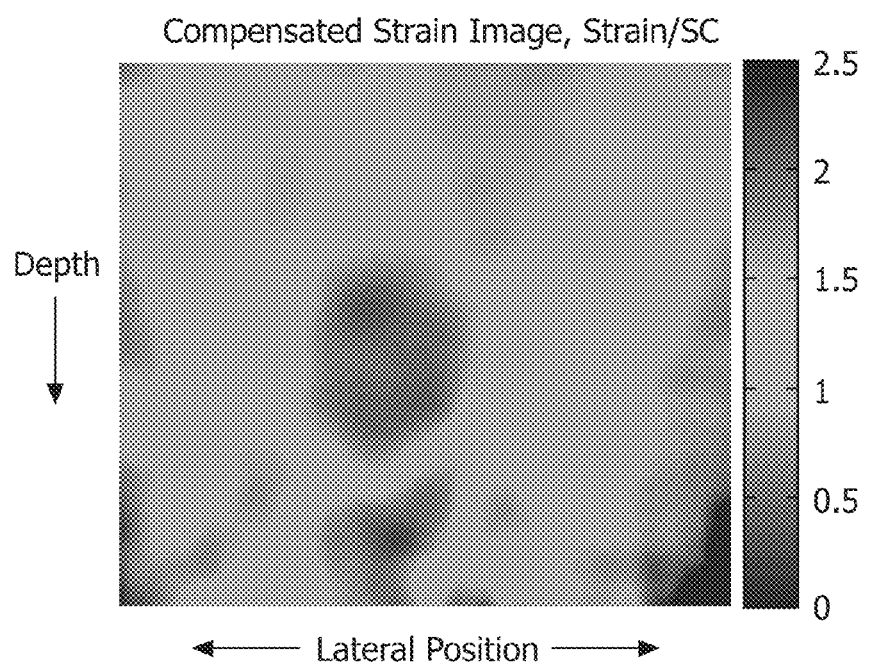
FIG. 9 is an elastogram showing an exemplary compensated strain image generated using the strain compensation function of FIG. 8.

Referring to FIG. 8, an image representative of a strain compensation function that can be generated by system 10 based upon median strain as a function of depth is shown. In FIG. 9, a compensated strain image generated by system 10 based upon the strain compensation function of FIG. 8 is shown. The tissue which has uniform properties and is surrounding the hard inclusion appears more uniform, drawing attention to the inclusion. In this example, the inclusion appears 2 to 3 times stiffer than the surrounding tissue in the image, where the actual stiffness is three times the surrounding tissue.

Figure 10:
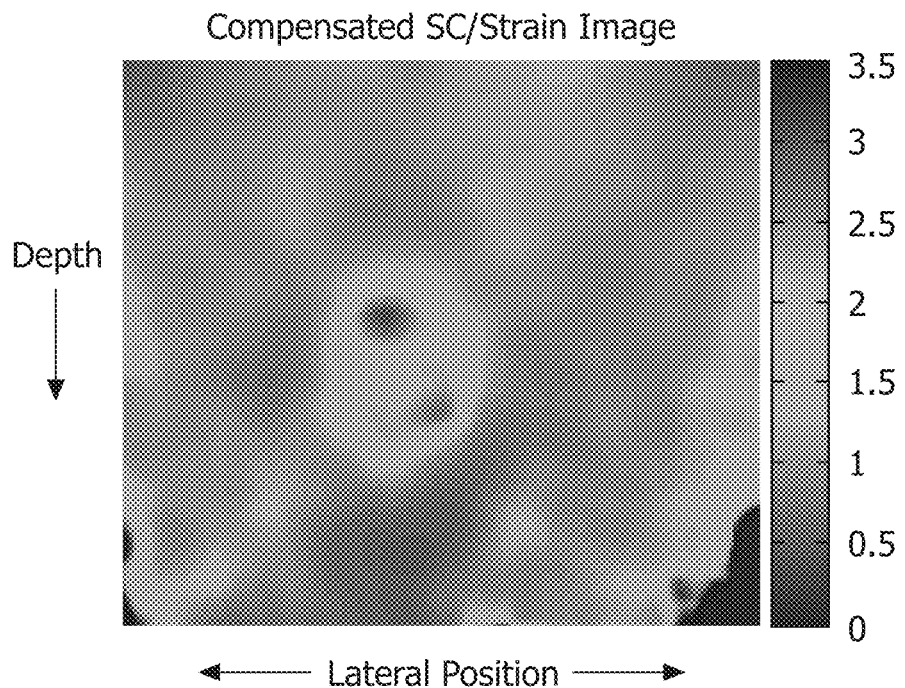
FIG. 10 is an elastogram showing the inverse of the compensated strain image of FIG. 9.

FIG. 10 shows the mathematical inverse of the compensated strain image of FIG. 9. The tissue surrounding the hard inclusion appears at a more uniform level, providing better contrast with the inclusion.

Figure 11:
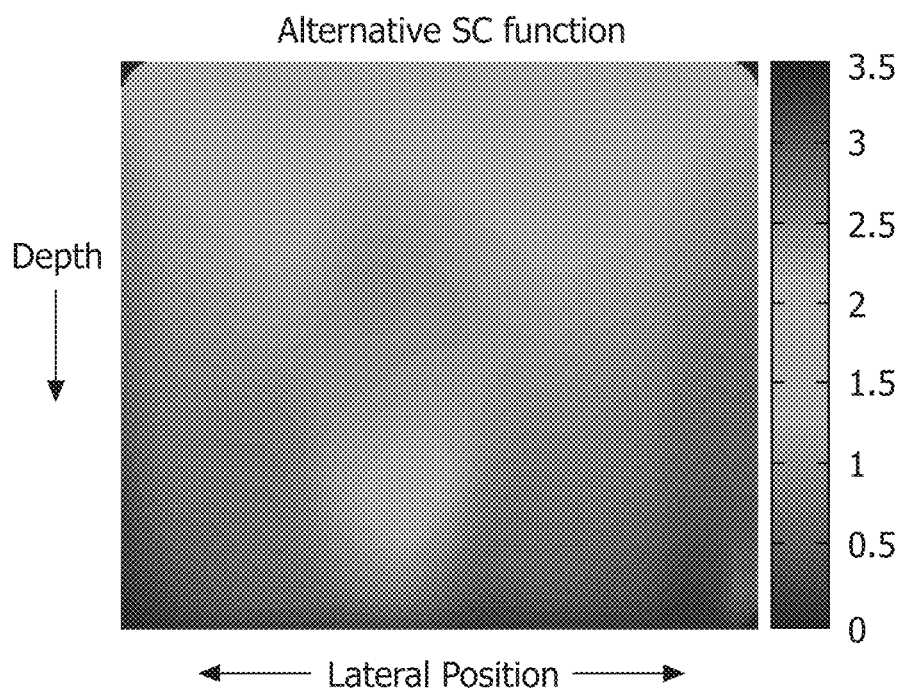
FIG. 11 is an image of another of a number of exemplary strain compensation functions generated according to the system or methods of FIGS. 1-5.
Figure 12:
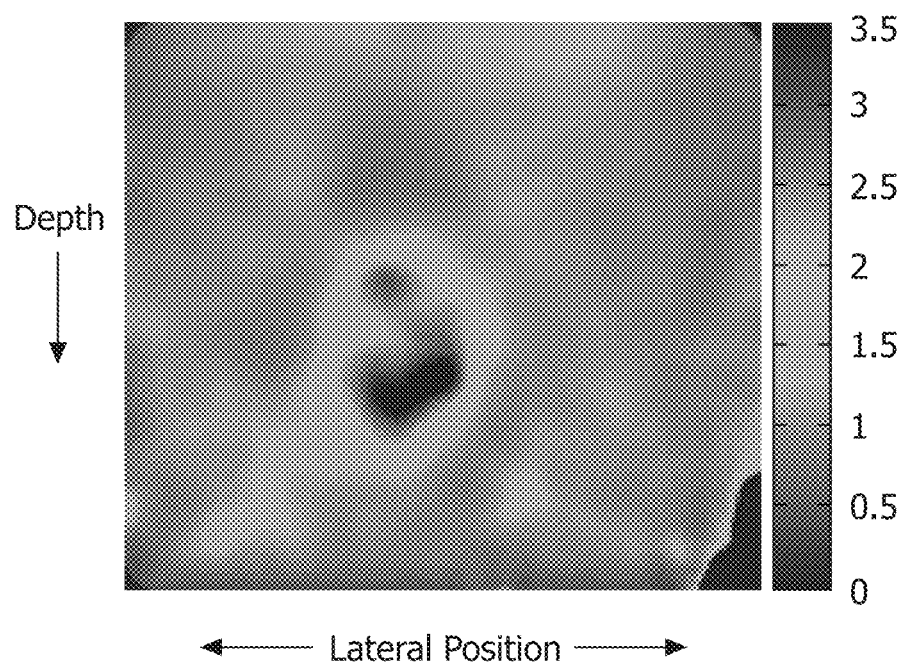
FIG. 12 is an elastogram showing an exemplary compensated strain image generated using the strain compensation function of FIG. 11.

Referring to FIG. 11, an image representative of another exemplary strain compensation function that can be generated by system 10 which varies both axially and laterally, so as to be 2-Dimensional, is shown. In FIG. 12, a compensated strain image generated by system 10 based upon the strain compensation function of FIG. 11 is shown.

System 10 can provide for qualitative imaging of strain based on a number of techniques including a user control to compensate strain as a function of depth, lateral and/or elevation positions; compensation of strain as a function of depth based upon predetermined compensation functions stored on the system; and/or adaptive compensation of strain images to account for non-uniform applied stress over a 2D or 3D field of view using the data captured during the examination. The methodology and system described herein is applicable to compensated strain images in either or both of 2D and 3D imaging.

Elastograms can include not only strain images but also other measurements related to tissue elasticity (e.g., ratio of lesion/normal tissues strain, Poisson's Ratio). Compensated strain images generated in accordance with the systems and methods of the present disclosure may not be directly displayed to users and can be further processed to produce elastograms.

The present disclosure contemplates the strain compensation function being based upon one or more of the following sources: user input (via controls); a priori data/model; current and past values of strain data. In addition, the methods of the exemplary embodiments can include presenting the strain data for display (image and/or graphical) and/or storage/export. In one embodiment, further processing of the data can be performed, including smoothing, remapping, (e.g., 1/compensated strain, Fn (compensated strain), and so forth), temporal persistence and any combination thereof. The imaging performed herein can include other techniques for either of both of 2-dimensional and 3-dimensional image data.

The invention, including the steps of the methodologies described above, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

The invention claimed is:

1. A method of elasticity imaging, the method comprising:
    transmitting ultrasonic energy and receiving echoes therefrom;
    processing imaging data from the echoes associated with an applied stress of a physiology of a patient;
    obtaining a strain compensation function associated with the applied stress, wherein the strain compensation function is configured to compensate for a strain variation that is not caused by an actual stiffness variation in the physiology of the patient;
    applying the strain compensation function to the imaging data to generate a compensated strain image; and
    presenting the compensated strain image, wherein the compensated strain image qualitatively highlights elastic differences in the physiology of the patient.

2. The method of claim 1, further comprising adjusting the strain compensation function based on user inputs, wherein the user inputs are based on expected results associated with a portion of the physiology.

3. The method of claim 1, further comprising determining the strain compensation function based on a strain compensation model generated prior to performing the elasticity imaging.

4. The method of claim 3, wherein the strain compensation model is generated based on at least one of (i) a mathematical model, (ii) data measured from a physical model, and (iii) data from an elasticity imaging of a different patient.

5. The method of claim 4, wherein the different patient has substantially uniform properties.

6. The method of claim 1, further comprising determining the strain compensation function based on at least a portion of the processed imaging data.

7. The method of claim 1, wherein the strain compensation function is determined based on a median strain calculated from the imaging data.

8. The method of claim 1, further comprising generating the applied stress by pressing a transducer against the patient in a region of the physiology, wherein the transducer transmits the ultrasonic energy and receives the echoes.

9. The method of claim 1, further comprising at least two of:
    (a) adjusting the strain compensation function based on user inputs with the user inputs being based on expected results associated with a portion of the physiology, (b) determining the strain compensation function based on a strain compensation model generated prior to performing the elasticity imaging, and (c) determining the strain compensation function based on at least a portion of the processed imaging data.

10. The method of claim 1, further comprising generating the compensated strain image in real-time.

11. A processor on which computer-executable code is executed, the computer-executable code configured to cause the processor to execute the steps of:
    processing ultrasound imaging data associated with an applied stress of a physiology of a patient;
    generating a strain compensation function associated with the applied stress based on at least one of (i) user inputs based on expected results associated with a portion of the physiology, (ii) a strain compensation model generated prior to processing the ultrasound imaging data, and (iii) at least a portion of the processed imaging data, wherein the strain compensation function is configured to compensate for a strain variation that is not caused by an actual stiffness variation in the physiology of the patient; and
    applying the strain compensation function to the imaging data to generate a compensated strain image, wherein the compensated strain image qualitatively highlights elastic differences in the physiology of the patient.

12. The processor of claim 11, further comprising computer-executable code for causing the computing device to present at least one of the compensated strain image and an inverse of the compensated strain image.

13. The processor of claim 11, wherein the strain compensation model is generated based on at least one of (i) a mathematical model, (ii) data measured from a physical model, and (iii) data from an elasticity imaging of a different patient.

14. The processor of claim 13, wherein the different patient has substantially uniform properties.

15. The processor of claim 11, wherein the strain compensation function is determined based on a median strain calculated from the imaging data.

16. The processor of claim 11, wherein the strain compensation function is generated based on two or more of (a) the user inputs, (b) the strain compensation model, and (c) the at least a portion of the processed imaging data.

17. An ultrasound imaging system comprising:
    a probe for transmitting ultrasonic energy into a physiology of a patient and receiving echoes;
    a display device; and
    a processor operably coupled to the probe and the display device,
    wherein the processor processes ultrasound imaging data associated with an applied stress of the physiology of the patient,
    wherein the processor generates a strain compensation function associated with the applied stress based on at least one of (i) user inputs based on expected results associated with a portion of the physiology, (ii) a strain compensation model generated prior to processing the ultrasound imaging data, and (iii) at least a portion of the processed imaging data, wherein the strain compensation function is configured to compensate for a strain variation that is not caused by an actual stiffness variation in the physiology of the patient,
    wherein the processor applies the strain compensation function to the imaging data to generate a compensated strain image, wherein the compensated strain image qualitatively highlights elastic differences in the physiology of the patient, and
    wherein the processor presents on the display device at least one of the compensated strain image and an inverse of the compensated strain image.

18. The system of claim 17, further comprising a compensation function control, wherein actuation of the compensation function control adjusts a magnitude of the strain compensation function.

19. The system of claim 17, further comprising a memory device, wherein one or more strain compensation models of the strain compensation function are stored in the memory device.

20. The system of claim 17, wherein the processor generates the compensated strain image in real-time.

* * * * *